United States Patent
Plant et al.

(10) Patent No.: US 6,484,569 B1
(45) Date of Patent: Nov. 26, 2002

(54) TUBE-IN-TUBE THERMAL EXCHANGER FOR LIQUID CHROMATOGRAPHY SYSTEMS

(75) Inventors: Kenneth R. Plant, Leominster, MA (US); Robert J. Dumas, Upton, MA (US)

(73) Assignee: Waters Investments Limited, New Castle, DE (US)

(*) Notice: Subject to any disclaimer, the term of this patent is extended or adjusted under 35 U.S.C. 154(b) by 0 days.

(21) Appl. No.: 09/698,417

(22) Filed: Oct. 27, 2000

(51) Int. Cl.$^7$ .................. B01D 15/08; G01N 31/08; G01N 21/41; G05D 23/24; F25B 29/00
(52) U.S. Cl. ..................... 73/61.57; 73/61.56
(58) Field of Search ............ 73/61.57, 61.56, 73/61.59, 23.25, 23.42; 210/656; 219/399; 96/106; 422/89

(56) References Cited

U.S. PATENT DOCUMENTS

| | | | |
|---|---|---|---|
| 3,440,864 A | 4/1969 | Blume | 73/61.1 |
| 3,483,986 A | 12/1969 | Wright | 210/198 |
| 4,284,352 A | 8/1981 | Carson et al. | 356/134 |
| 4,589,477 A | 5/1986 | Scott | 165/66 |
| 4,598,765 A | 7/1986 | Atwood et al. | 165/66 |
| 4,670,141 A | 6/1987 | Shackleford et al. | 210/198.2 |
| 4,861,473 A | 8/1989 | Shackleford et al. | 210/198.2 |
| 5,013,433 A | 5/1991 | Shalon | 210/198.2 |
| 5,032,283 A | 7/1991 | Scott et al. | 210/656 |

*Primary Examiner*—Daniel S. Larkin
*Assistant Examiner*—David J. Wiggins
(74) *Attorney, Agent, or Firm*—Scully, Scott, Murphy & Presser; Brian Michaelis

(57) ABSTRACT

A thermal exchanger for a liquid chromatography system is provided. The tube-in-tube thermal exchanger comprises a first and a second sections of tubing, a first connector and a second connector. The first section of tubing carries sample solution from the packed chromatography column. The second tubing carries the sample solution from the detector out of the system, i.e., in an opposite direction to the direction of the first section of tubing. Both the first section of tubing and the second section of tubing connect to the first connector, which combines the two sections of tubing into a thermal exchange tubing. The thermal exchange tubing comprises the first section of tubing placed inside the second section of tubing such that waste fluid from the second tubing can optimally exchange thermal energy with fluid from the chromatography column. The thermal exchange tubing is configured into a plurality of coils. The number of coils in the thermal exchange tubing is specific to the chromatography application and is determined by various parameters including the composition of the sample solution, estimated temperature gradient, fluid flow rates and heat transfer coefficient. The thermal exchanger provides stabilized temperature fluid to a detector with minimal volume into the flow path between the chromatography column and the detector.

25 Claims, 2 Drawing Sheets

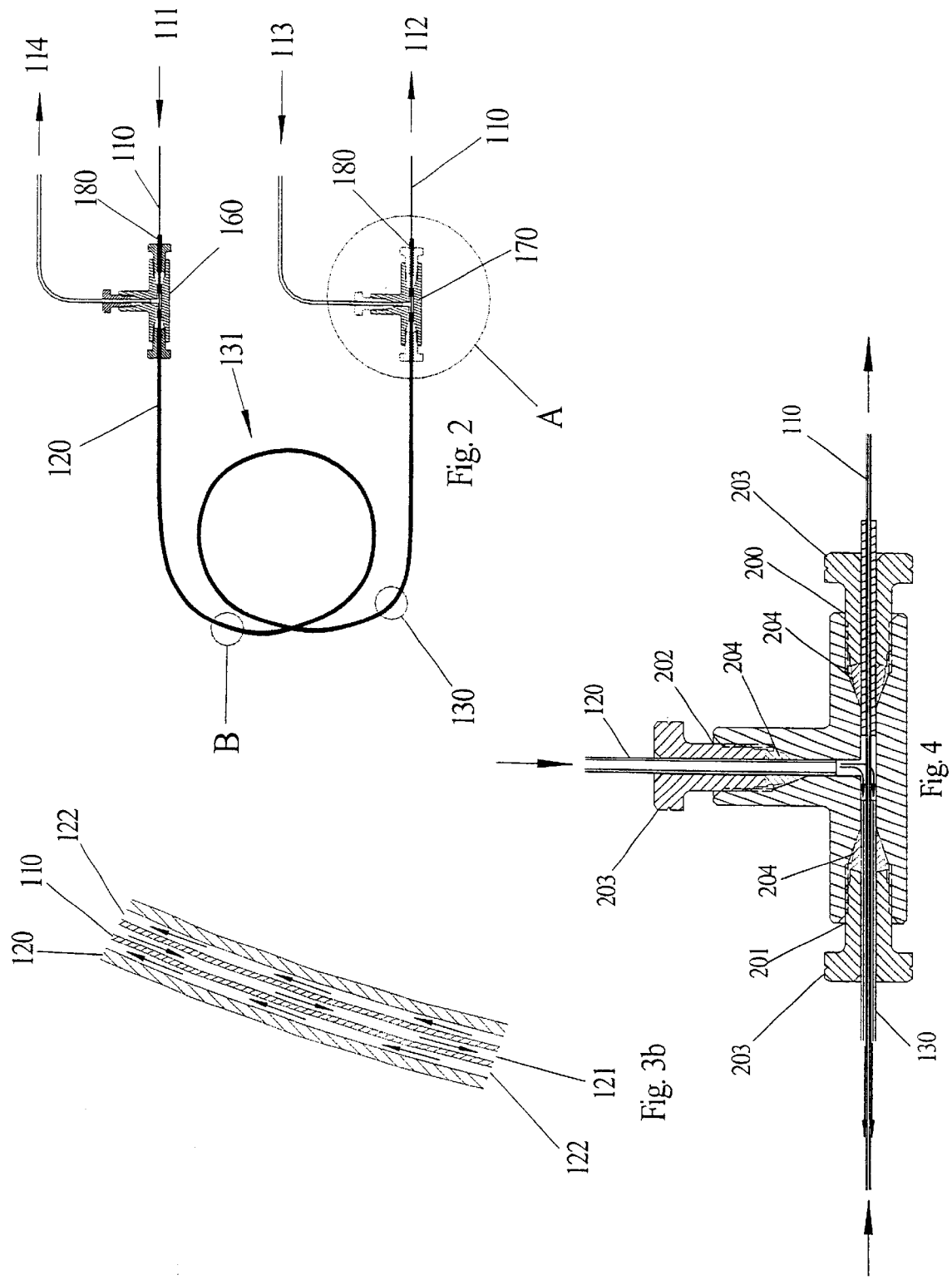

TUBE-IN-TUBE THERMAL EXCHANGER FOR LIQUID CHROMATOGRAPHY SYSTEMS

FIELD OF THE INVENTION

The present invention relates to thermal exchangers and more specifically to thermal exchangers capable of delivering a sample solution at a specified temperature to a detector for liquid chromatography systems.

BACKGROUND

Liquid chromatography systems are well known for analyzing sample solutions made up of different chemical compounds. Typically, a liquid chromatography system includes a chromatography column packed with packing material, a detector for analyzing the sample solution, a section of tubing for carrying the sample solution from the chromatography column to the detector, and a section of tubing for carrying the sample solution from the detector and out of the chromatography system.

The operation of a liquid chromatography system can be generally described as follows. A liquid solvent is pumped into the chromatography system at high pressure. At a point in the chromatography system ahead of the chromatography column, the sample solution is injected into the system and carried forward with the liquid solvent. Eventually, the sample solution reaches the packed chromatography column and begins to flow through it. Because each of the chemical compounds which make up the sample solution reacts differently with the packing material in the chromatography column, the various chemical compounds flow through the packed column at different rates. Thus, the different chemical compounds in the sample solution separate out as individual peaks in concentration as the sample solution flows through the chromatography column. From the packed chromatography column, the separated chemical compounds proceed to the detector where they are analyzed. In the detector, some physical characteristic of the compounds is measured to identify the chemical composition of the peaks in the liquid solvent.

One type of detector utilized in liquid chromatography systems is a refractive index detector. Refractive index detectors measure the difference in refractive index of a two fluids and typically consist of a light emitting diode (LED), a flow cell having a sample side and a reference side, and a dual element photodiode detector. The refractive index of a fluid is highly dependent on the temperature of the fluid. Even slight variations in the temperature of a fluid drastically affect the refractive index of the fluid. For this reason, refractive index detectors are often fitted with temperature-controlled ovens within which the above detector elements reside. The oven is typically set to a temperature higher than the ambient temperature or surrounding environment temperature to insure control within narrow limits.

Often times, the sample solution exits the packed chromatography column at temperatures significantly higher or lower than the detector oven temperature. Because the refractive index of a fluid is so highly dependent on the temperature of the fluid, liquid chromatography systems that utilize refractive index detectors or other similar detectors must include special heat exchangers in order to provide meaningful results. The special heat exchangers insure the sample solution received by the refractive index detector is at a stable temperature within narrow limits. The present invention is a special tube-in-tube heat exchanger which uses fluid counterflow to exchange thermal energy between the incoming sample solvent and the outgoing waste solvent. This exchange of thermal energy automatically raises or lowers the temperature of the incoming sample fluid to a value very close to that of the detector oven. Outgoing fluid is already at the same temperature as that of the oven and provides the proper amount of thermal energy to the incoming fluid. In this way, the incoming fluid can more easily be stabilized to the exact oven temperature by the next stage heat exchanger attached to the optical bench assembly inside the detector oven.

In addition to insuring the sample solution is presented to the detector at a stable temperature, a heat exchanger utilized in a liquid chromatography system that includes a refractive index detector or other similar detector must introduce minimal volume into the flow path between the chromatographic column and the detector. If the heat exchanger introduces too much volume into the flow path between the chromatography column and the detector, there is a high probability that the constituent compound peaks that were separated in the chromatography column will be distorted and made less distinct. To the extent any previously separated compound peaks are made less distinct, the performance of the liquid chromatography system is adversely affected.

Thermal exchangers like the one disclosed in U.S. Pat. No. 4,284,352 entitled "Heat Exchanger for Refractometer" issued to Carson have been used previously in liquid chromatography systems. The Carson thermal exchanger is less than ideal for several reasons. One major problem with the Carson exchanger is that it is very difficult to manufacture, Four steps are required to manufacture the heat exchanger. First, four stainless steel tubes must be formed into a bundle. Second, the bundled tubes must be lashed or wrapped together with wire. Third, the tube bundle must be plated with copper so that the stainless steel tubes will accept solder. And fourth, the plated tubes must be dipped in solder to form a thermal contact path among the tubes.

An additional problem with the Carson heat exchanger is that it cannot be modified or repaired once it is manufactured. The heat exchanger is a permanent soldered assembly. If one of the tubes breaks or get clogged, the entire heat exchanger must be replaced.

SUMMARY

The present invention provides a thermal exchanger capable of providing a fluid whose temperature has been brought very close to that of a desired stable temperature setpoint within a detector. The thermal exchanger introduces minimal volume into the flow path between the chromatography column and the detector. The thermal exchanger of the present invention is easy to manufacture, repair and it is modifiable.

According to the present invention, in a liquid chromatography system including a chromatography column packed with packing material and a detector, a thermal exchanger comprises a first and second section of tubing, a waste T connector and a sample T connector. The first section of tubing carries sample solution from the packed chromatography column. The second section carries the sample solution from the detector out of the system. Both the first section of tubing and the second section of tubing connect to the first T connector. From the first T connector, a third section of tubing emerges. The third section of tubing comprises the first section of tubing placed inside the second section of tubing such that waste fluid can exchange thermal energy with fluid from the chromatography column. The third section of tubing is wrapped into a plurality of coils. The number of coils in the third section of tubing depends on the specific chromatography application. The present invention provides a thermal exchanger capable of adjusting a high or low temperature incoming fluid to a stable temperature close to a desired temperature at a detector. The present invention also introduces minimal volume into the flow path between the chromatography column and the detector.

An advantage of the present invention is its ability to deliver sample solution at a desired, stabilized temperature to a detector where the sample solution is analyzed.

A minimal amount of additional volume is introduced into the flow path between a chromatography column and a detector. Another advantage of the present invention is that it is easy to manufacture, repair and it is modifiable.

Another advantage of the thermal exchanger according to the present invention is that it provides optimal thermal contact between sample solution coming into the chromatography system and sample solution exiting the sample solution.

BRIEF DESCRIPTION OF THE DRAWINGS

The foregoing and other features and advantages of the present invention will be more fully understood from the following detailed description of illustrative embodiments, taken in conjunction with the accompanying drawings in which:

FIG. 2 shows a thermal exchanger according to the present invention;

FIG. 3b is an enlargement of portion B of FIG. 2 that is a cross sectional view of the thermal exchange tubing where fluid counterflow takes place; and FIG. 4 is an enlargement of portion A of FIG. 2 that shows a T connector used in the present invention.

DETAILED DESCRIPTION

Figure 1:
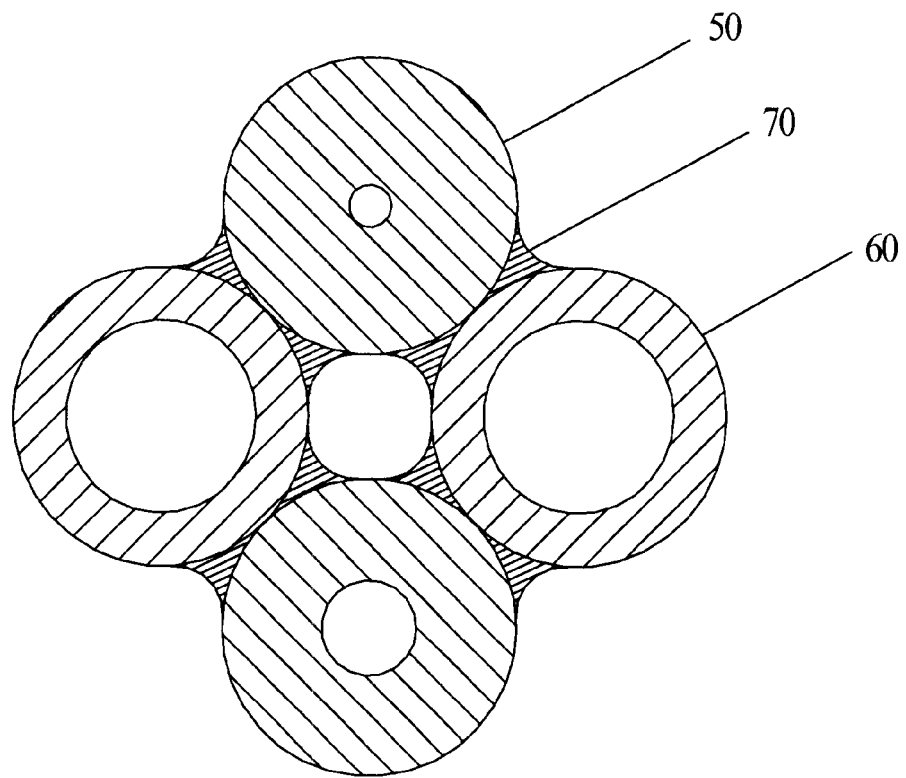
FIG. 1 shows a tube configuration in a prior art heat exchanger.

Referring in detail to the drawings, FIG. 1 shows a tube configuration in a prior art heat exchanger utilized with a chromatography system including a chromatography column and a detector. Tube 50 carries sample solution from the chromatography column to the detector, and tube 60 carries sample solution from the detector and out of the system. Only a small portion of tube 50 and tube 60 are in physical contact aided by solder 70. Furthermore, thermal energy must travel through the thick wall of the inlet tube 50. Consequently, the amount of thermal exchange occurring between the solutions in tube 50 and tube 60 is less than optimal.

Referring now to FIG. 2 the heat exchanger according to the present invention is shown. The thermal exchanger of the illustrative embodiment comprises a inner tubing 110, a outer tubing 120, a waste T connector 160, and a sample T connector 170. The inner tubing 110 of the illustrative embodiment is a stainless steel tube having an outside diameter of approximately 0.02 in and an interior diameter of approximately 0.010 in. The inner tube 110 may be fashioned with other materials known in the art as long as they are inert to the sample and solvents used within the chromatography system and posses good thermal exchange properties. The outer tubing 120 in the illustrative embodiment is a stainless steel tube having an outside diameter of approximately 0.06 in. and an interior diameter of approximately 0.04 in. The outer section of tubing may also be fashioned with other materials known in the art as long as they are inert to the sample and solvents used within the chromatography system.

The inner tubing 110 is positioned within the outer tubing 120 simply by random intermittent contact of the outer surface of the inner tube 110 with the inner surface of the outer tube 120. This random positioning aids the mutual thermal energy transfer between the tubes by ensuring a degree of meandering flow of the fluid in the channel created by the tube-within-a-tube. The placement of the inner tubing 110 within the outer tubing 120 results in a thermal exchange tubing 130. The thermal exchange tubing 130 can be of varied lengths depending on the specific application and the degree of thermal exchange needed within that application. The thermal exchange tubing 130 within the illustrative embodiment has a coil 131 as illustrated in FIG. 2 to allow for a suitable thermal exchange surface area within an economy of space. The number of coils 131 is determined by the following factors: the composition of the sample solution, the estimated temperature gradient between the sample solution exiting the packed chromatography column and the sample solution leaving the detector, the flow rate of the fluid exiting the packed chromatography column, the flow rate of the fluid leaving the detector, and the heat transfer coefficient.

Figure 3A:
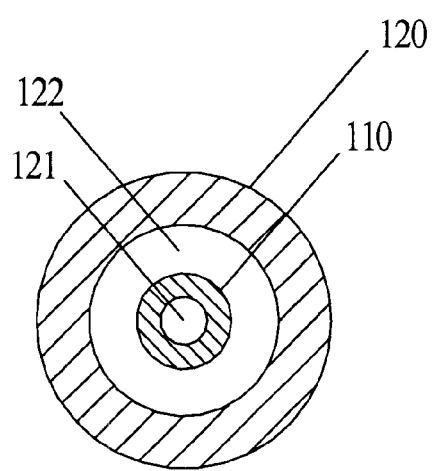
FIG. 3a is an end view of the thermal exchange tubing showing the region where fluid counterflow takes place.

Referring to FIGS. 3a and 3b, the thermal exchange tubing 130 in the illustrative embodiment has a first fluid flow channel 121 and a second fluid flow Channel 122. The interior diameter of the inner tubing 110 creates the first fluid flow channel 121. The first fluid flow channel 121 carries the sample solution which is to be analyzed from the liquid chromatography column in a loop that flows from a sample fluid inlet 111 through the first fluid flow channel 121 to a next stage 112. The outer section of tubing 120 carries a fluid flow from a flow cell 113 through the second fluid flow channel 122 formed from the interior diameter of the outer tubing 120 and the outer diameter of the inner tubing 110. The outer section of tubing 120 carries a fluid through the second fluid flow channel 122 from a flow cell 113 through the channel 122 to a waste 114.

As shown in FIG. 3b, the thermal properties of the solution in the second flow channel 122 are exchanged with the thermal properties of the solution contained within the first channel 121. The inner tubing 110 is surrounded by the solution flowing through the second flow channel 122, creating a large area of surface contact. Thus thermal exchange between the fluid in the first flow channel 121 and the second flow channel 122 provides optimal thermal transfer between the solution exiting the chromatography column and the solution leaving the detector. The optimal heat transfer insures that the sample solution flowing into the detector closely approximates the specified temperature.

As shown in FIG. 2, the inner tubing 110 and the outer tubing 120 are connected to the thermal exchange tubing 130 and the chromatography system by the use of a waste T connector 160 and a sample T connector 170. A plastic sleeve 180 is placed around the outer diameter of the inner section of tubing 110. The plastic sleeve 180 increases the outer diameter of the inner section of tubing 110 to substantially the same outer diameter of the outer section of tubing 120. The plastic sleeve 180 allows the use of the same fluid connections within the sample T connector 170 and the waste T connector 160. The plastic sleeve 180 also acts as a seal around the inner section tubing 110.

The sample T connector 170 creates a fluid connection between the thermal exchange tubing 130 and the outer section tubing 120. The sample T connector 170 allows the outer section tubing 120 carrying fluid from the flow cell 113 to be in fluidic communication with the second flow channel 122. The waste T connector 160 also creates a fluid connection with the thermal exchange tubing 130 and allows the fluid from the flow cell 113 contained within the second flow channel 122 to be in fluidic communication to the waste 114. The first inner section of tubing 110 passes through both the waste connector 160 and the sample connector 170.

FIG. 4 illustrates an enlarged view of a T connector used in the illustrative embodiment. The T connector has a first port 200, a second port 201 and a third port 202. Each port has a compression screw 203. The compression screws have a ferrule 204. The ferrules 204 are configured to receive the thermal exchange tubing 130 that is formed from the inner tubing 110 to be placed within the outer tubing 120. In the illustrative embodiment the ferrules 204 are made of stainless steel. The T connectors utilized in the illustrative embodiment are commercially available from Upchurch Scientific of Chicago Ill. Other connectors known in the art may be utilized that allow for the tube within the tube fluid flow. Other sleeves 180 and compression ferules 204 may be used that are known in the art that are compatible with the connectors utilized.

The configuration of the heat exchanger is important because it determines the character of the peaks produced by the chromatography system. The peaks produced by the chromatography system are directly related to the lengths of the different sections of tubing and the number of coils present in the heat exchanger. Decreasing the length of the different sections of tubing in the heat exchanger can produce sharper peaks. However, decreasing the length of the different sections of tubing also limits the amount of heat transfer that can take place between the solution exiting the chromatography column and the solution leaving the detector. If a sample solution is leaving a chromatography column at a very high temperature, it may be necessary to build a thermal exchanger with longer sections of tubing to insure the proper amount of thermal exchange takes place. Otherwise, the sample solution may not enter the detector at the appropriate temperature.

In general, the dimensions of the thermal exchanger elements are determined by the particular chromatography application. For example, in analytic chromatography, the fluid flow rates used are within a relatively narrow range of values and the selection of solvents is such that a single predetermined length dimension for the thermal exchanger may be selected.

In micro-bore chromatography, flow rates may be reduced relative to those used for analytic chromatography and a reduced length for the thermal exchanger may be appropriate.

And in preparatory chromatography where flow rates are usually much higher than those used in analytic chromatography, an entirely different set of thermal exchanger dimensions may be appropriate.

Although the thermal exchange tubing described in the illustrative embodiment herein is stainless steel it should be appreciated that other tubing could be implemented for one or more of the tubing components such as titanium, or the like.

Although the thermal exchange tubing described in the illustrative embodiment is of circular cross section and certain dimensions, it should be appreciated by those skilled in the art that for other applications alternative geometries and dimensions can be implemented.

Although the present invention has been shown and described with respect to illustrative embodiments thereof, various changes, omissions and additions in the form and detail thereof may be made therein without departing from the spirit and scope of the invention.

What is claimed is:

1. In a liquid chromatography system, a thermal exchanger for providing a sample solution to a detector at or near a specified stable temperature within specified limits comprising:

a first section of tubing configured to carry sample solution in a first direction;

a second section of tubing configured to carry sample solution in a second opposite direction;

a first connector that receives said first section of tubing and said second section of tubing and combines them into one section of tubing;

a third section of tubing which emerges from said first connector comprising said first section of tubing placed inside of said second section of tubing; and a second connector which receives said third section of tubing and splits it back into said first section of tubing and said second section of tubing.

2. A thermal exchanger according to claim 1 where said tubing is stainless steel.

3. A thermal exchanger according to claim 1 where said detector is a refractive index detector.

4. A thermal exchanger according to claim 1 wherein said third section of tubing is wrapped into a plurality of coils.

5. A thermal exchanger according to claim 1 where said first and second connectors contain a means to allow a first fluid to exchange thermal properties with a second fluid where said fluids are not cross contaminated.

6. A thermal exchanger according to claim 4 where a number of the coils is determined by: (1) composition of the sample solution; (2) estimated temperature gradient between the sample solution exiting a packed chromatography column and the sample solution leaving the detector; (3) flow rate of fluid exiting the packed chromatography column; (4) flow rate of fluid leaving the detector; and (5) the heat transfer coefficient of said thermal exchanger.

7. In a liquid chromatography system consisting of a chromatography column packed with packing material and a detector, a heat exchanger for providing sample solution to the detector at a specified temperature comprising:

a first section of tubing for carrying sample solution from the chromatography column; a second section of tubing for carrying sample solution from the detector;

a first T connector that receives said first section of tubing and said second section of tubing and combines them into one section of tubing;

a third section of tubing which emerges from said first T connector comprising said first section of tubing placed inside of said second section of tubing, said third section of tubing is wrapped into a plurality of coils; and a second T connector which receives said third section of tubing and splits it back into said first section of tubing and said second section of tubing.

8. A method for producing a tube-in-tube thermal exchanger for a liquid chromatography system including a packed chromatography column and a detector, the method comprising the following steps:

placing a first section of tubing inside of a second section of tubing to produce a third section of tubing, the first section of tubing for carrying sample solution in a first direction from the packed chromatography column and the second section of tubing for carrying sample solution in a second and opposite direction from the detector;

wrapping the third section of tubing into a plurality of coils; and splitting the third section of tubing back into the first section of tubing and the second section of tubing.

9. The method according to claim 8 where a number of coils in the third section is determined by: (1) composition of the sample solution; (2) estimated temperature gradient between the sample solution exiting the packed chromatography column and the sample solution leaving the detector; (3) flow rate of fluid exiting the packed chromatography column; (4) flow rate of fluid leaving the detector; and (5) the heat transfer coefficient of said thermal exchanger.

10. In a liquid chromatography system comprising a packed chromatography column and a detector, a thermal exchanger for providing a sample solution to the detector at or near a specified stable temperature within specified limits, the thermal exchanger comprising:

a thermal exchange tubing comprising a first section of tubing carrying sample solution from the packed chromatography column to the detector in a first direction and a second section of tubing carrying sample solution from the detector out of the chromatography system in a second and opposite direction, the first section of tubing placed inside the second section of tubing for exchanging thermal energy between fluid in the first section of tubing and fluid in the second section of tubing.

11. A thermal exchanger according to claim 10 where said tubing is stainless steel.

12. A tube-in-tube thermal exchanger according to claim 10 where said detector is a refractive index detector.

13. A thermal exchanger according to claim 10 where said thermal exchange tubing is wrapped into a plurality of coils.

14. A thermal exchanger according to claim 10 further comprising a first connector for receiving said first section of tubing and said second section of tubing and combining them into said thermal exchange tubing.

15. A thermal exchanger according to claim 14 further comprising a second connector for receiving said thermal exchange tubing and splitting it into said first section of tubing and said second section of tubing.

16. A thermal exchanger according to claim 15 where said first connector and said second connector comprise a means for allowing fluid in said first section of tubing to exchange thermal properties with fluid in said second section of tubing where said fluids are not cross contaminated.

17. A thermal exchanger according to claim 15 where said first connector and said second connector are T connectors.

18. A thermal exchanger according to claim 13 where a number of said coils in said thermal exchange tubing is determined by: (1) composition of the sample solution; (2) estimated temperature gradient between the sample solution exiting the packed chromatography column and the sample solution leaving the detector; (3) flow rate of fluid exiting the packed chromatography column; (4) flow rate of fluid leaving the detector; and (5) the heat transfer coefficient of said thermal exchanger.

19. A thermal exchanger according to claim 1 where said first connector and said second connector are T connectors.

20. A heat exchanger according to claim 7 where said tubing is stainless steel.

21. A heat exchanger according to claim 7 where said detector is a refractive index detector.

22. A heat exchanger according to claim 7 where said first and second T connectors contain a means to allow a first fluid to exchange thermal properties with a second fluid where said fluids are not cross contaminated.

23. A thermal exchanger according to claim 1 where said first section of tubing has an inside diameter of approximately 0.01 inches and an outside diameter of approximately 0.02 inches and said second section of tubing has an inside diameter of approximately 0.04 inches and an outside diameter of approximately 0.06 inches.

24. A heat exchanger according to claim 7 where said first section of tubing has an inside diameter of approximately 0.01 inches and an outside diameter of approximately 0.02 inches and said second section of tubing has an inside diameter of approximately 0.04 inches and an outside diameter of approximately 0.06 inches.

25. In a liquid chromatography system comprising a chromatography column and a detector, a tube-in-tube thermal exchanger for providing a sample solution to said detector at or near specified stable temperature within specified limits, the thermal exchanger comprising:

a first section of tubing configured to carry sample solution in a first direction from said chromatography column;

a second section of tubing configured to carry sample solution in a second and opposite direction from said detector;

a first connector that receives said first section of tubing and said second section of tubing and combines them into one section of tubing;

a third section of tubing which emerges from said first connector comprising said first section of tubing placed inside said second section of tubing, said first section of tubing having an inside diameter of approximately 0.01 inches and an outside diameter of approximately 0.02 inches and said second section of tubing having an inside diameter of approximately 0.04 inches and an outside diameter of approximately 0.06 inches; and a second connector which receives said third section of tubing and splits it back into said first section of tubing and said second section of tubing.

* * * * *